US012653471B2

(12) United States Patent
Otaki et al.

(10) Patent No.: US 12,653,471 B2
(45) Date of Patent: Jun. 16, 2026

(54) RADIATION DETECTION APPARATUS COMPRISING A RADIATION DETECTOR, A CONDUCTIVE BASE SUPPORTING THE RADIATION DETECTOR, A CIRCUIT BOARD, AND AN INSULATING MEMBER

(71) Applicant: Konica Minolta, Inc., Tokyo (JP)

(72) Inventors: Junichiro Otaki, Hachioji (JP); Hajime Ishimoto, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 165 days.

(21) Appl. No.: 18/589,558

(22) Filed: Feb. 28, 2024

(65) Prior Publication Data

US 2024/0302544 A1     Sep. 12, 2024

(30) Foreign Application Priority Data

Mar. 8, 2023     (JP) ................................. 2023-035402

(51) Int. Cl.
*A61B 6/42*          (2024.01)
*G01T 1/20*          (2006.01)

(52) U.S. Cl.
CPC ........ *G01T 1/20182* (2020.05); *A61B 6/4283* (2013.01); *G01T 1/20184* (2020.05)

(58) Field of Classification Search
CPC ....... A61B 6/42; A61B 6/4208; A61B 6/4233; A61B 6/4258; A61B 6/4266; A61B 6/4283; G01T 1/20; G01T 1/2006; G01T 1/2018; G01T 1/20182; G01T 1/20184; G01T 1/20186; G01T 1/20187; G01T 1/20188; G01T 1/24; G01T 1/241; G01T 1/243; G01T 1/244; G01T 1/247; G01T 1/248
USPC ...................................... 250/370.09; 378/98.8
See application file for complete search history.

(56) References Cited

U.S. PATENT DOCUMENTS

| | | | |
|---|---|---|---|
| 7,247,860 B2 * | 7/2007 | Yanagita ............... | G01T 1/2928 |
| | | | 250/370.09 |
| 7,420,178 B2 * | 9/2008 | Tokuda ................. | H10F 39/195 |
| | | | 250/370.09 |
| 7,442,939 B2 * | 10/2008 | Yagi ........................ | G01T 1/247 |
| | | | 250/370.11 |
| 7,989,772 B2 * | 8/2011 | Yagi ....................... | G01T 1/2006 |
| | | | 250/370.09 |
| 8,044,360 B2 * | 10/2011 | Kitada .................... | G01T 1/241 |
| | | | 250/370.08 |
| 8,366,319 B2 * | 2/2013 | Kawasaki ............... | G01T 1/244 |
| | | | 378/189 |
| 8,440,977 B2 * | 5/2013 | Ishii .................... | H10F 39/1898 |
| | | | 250/370.08 |

(Continued)

FOREIGN PATENT DOCUMENTS

JP          2012073186 A      4/2012

*Primary Examiner* — Allen C. Ho
(74) *Attorney, Agent, or Firm* — CANTOR COLBURN LLP

(57)          ABSTRACT

A radiation detection apparatus includes: a radiation detector that detects radiations; a conductive base that supports the radiation detector; a circuit board that includes a first ground electrode and a second ground electrode different from the first ground electrode, and processes a signal read from the radiation detector, and an insulating member that blocks electrical connection between the second ground electrode and the base.

8 Claims, 6 Drawing Sheets

(56) References Cited

U.S. PATENT DOCUMENTS

| | | | | |
|---|---|---|---|---|
| 8,513,633 B2 * | 8/2013 | Koyanagi | ................. | G01T 1/16 |
| | | | | 250/584 |
| 8,581,202 B2 * | 11/2013 | Yamada | .............. | G01T 1/20188 |
| | | | | 250/370.15 |
| 10,481,280 B2 * | 11/2019 | Ichimura | ............... | G01T 1/2928 |
| 12,111,430 B2 * | 10/2024 | Horiuchi | ................... | G01T 1/24 |
| 12,169,261 B2 * | 12/2024 | Aida | ................... | G01T 1/20184 |
| 12,468,052 B2 * | 11/2025 | Bombelli | .............. | G01T 1/2928 |

* cited by examiner

RADIATION DETECTION APPARATUS COMPRISING A RADIATION DETECTOR, A CONDUCTIVE BASE SUPPORTING THE RADIATION DETECTOR, A CIRCUIT BOARD, AND AN INSULATING MEMBER

CROSS-REFERENCE TO RELATED APPLICATIONS

The present invention claims priority under 35 U.S.C. § 119 to Japanese Patent Application No. 2023-035402, filed on Mar. 8, 2023, the entire content of which is incorporated herein by reference.

BACKGROUND

Technical Field

The present invention relates to a radiation detection apparatus.

Description of the Related Art

Conventionally known is a radiation detection apparatus that irradiates an object with radiation and detects an intensity distribution of the radiation transmitted through the object, and the radiation detection apparatus has been widely used in the medical field, the industrial field, and the like. In recent years, portable (cassette-type) radiation detection apparatuses that can be separated from an imaging table and carried have been developed and put into practical use. Such a radiation detection apparatus is sometimes referred to as a flat panel detector (FPD) because the radiation detection apparatus has a panel shape. The FPD includes a radiation detector for detecting radiations.

The above-described portable radiation detection apparatus is required to be thin and lightweight so that a technician can carry the radiation detection apparatus to an imaging position. However, in order to achieve a reduction in thickness and weight, it is necessary to perform design in consideration of an influence of electrical noises on an image due to low-profile high-density packaging.

Then, a configuration has been disclosed in which a radiation detection panel (TFT) is covered with a conductive member, and the panel is fixed to a constant potential to function as a shield, thereby making it possible to reduce electrical noises on the radiation detection panel (for example, see JP 2012-73186A).

In general, an electric circuit that drives the radiation detection panel has a plurality of potentials for different purposes. Examples of the plurality of potentials include a potential serving as a reference for a digital signal such as an image, and a potential serving as a reference when an analog device is driven. A plurality of circuit boards constituting the electric circuit are provided with a plurality of electrodes set to each of a plurality of potentials.

In a case where the circuit board that receives an image signal from the radiation detection panel is divided into a plurality of circuit boards, the potentials that should be the same may be different among the circuit boards. When the potentials that should be the same are different among the circuit boards, a difference occurs in the level of the image signal and the operation of the device. Since the difference occurs, unevenness occurs in the image. Therefore, the electrodes having the same potential are connected to each other among the circuit boards using a connecting member, thereby stabilizing the potential. The connecting member and the circuit board are fastened together to a base and brought into pressure contact with each other using an attachment screw for attaching the circuit board to the base, thereby ensuring reliable electrical connection between the potential electrode and the connecting member.

SUMMARY OF THE INVENTION

In recent years, in order to improve strength against a load and an impact without increasing the weight, study has been made on the use of a conductive metal such as Mg for a base in a portable radiation detection apparatus. However, as illustrated in FIG. 8, when a base 112 is made of metal, attachment screws 133 and a connecting member 132 on a back surface side of a circuit board 114 contact the base 112. Due to the contact, a ground (R-GND) G101 and a ground (G-GND) G102 that are set to a plurality of potentials for different purposes are electrically connected to each other. When the ground G101 and the ground G102 that are set to a plurality of potentials for different purposes are electrically connected to each other, image unevenness occurs. The occurrence of image unevenness is caused by reasons such as an unintended mixture of noises. A conventional base that supports a plurality of circuit boards is made of a non-conductive resin. The base made of a resin is insulated from the circuit board and the attachment screw without any particular measure.

The configuration described in JP 2012-73186 is a configuration in which the base having a metal layer and a ground of the circuit are electrically connected but is not a configuration in which a plurality of potentials for different purposes are provided on the circuit board. Therefore, there is no fact that a plurality of potentials for different purposes are electrically connected to each other.

An object of the present invention is to provide a radiation detection apparatus capable of preventing occurrence of image unevenness even in a configuration in which a plurality of potentials for different purposes are provided on a circuit board.

To achieve at least one of the abovementioned objects, according to an aspect of the present invention, a radiation detection apparatus reflecting one aspect of the present invention includes:

a radiation detector that detects radiations;

a conductive base that supports the radiation detector;

a circuit board that includes a first ground electrode and a second ground electrode different from the first ground electrode, and processes a signal read from the radiation detector; and an insulating member that blocks electrical connection between the second ground electrode and the base.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION

Hereinafter, one or more embodiments of the present invention will be described with reference to the drawings. However, the scope of the invention is not limited to the disclosed embodiments.

Figure 1:
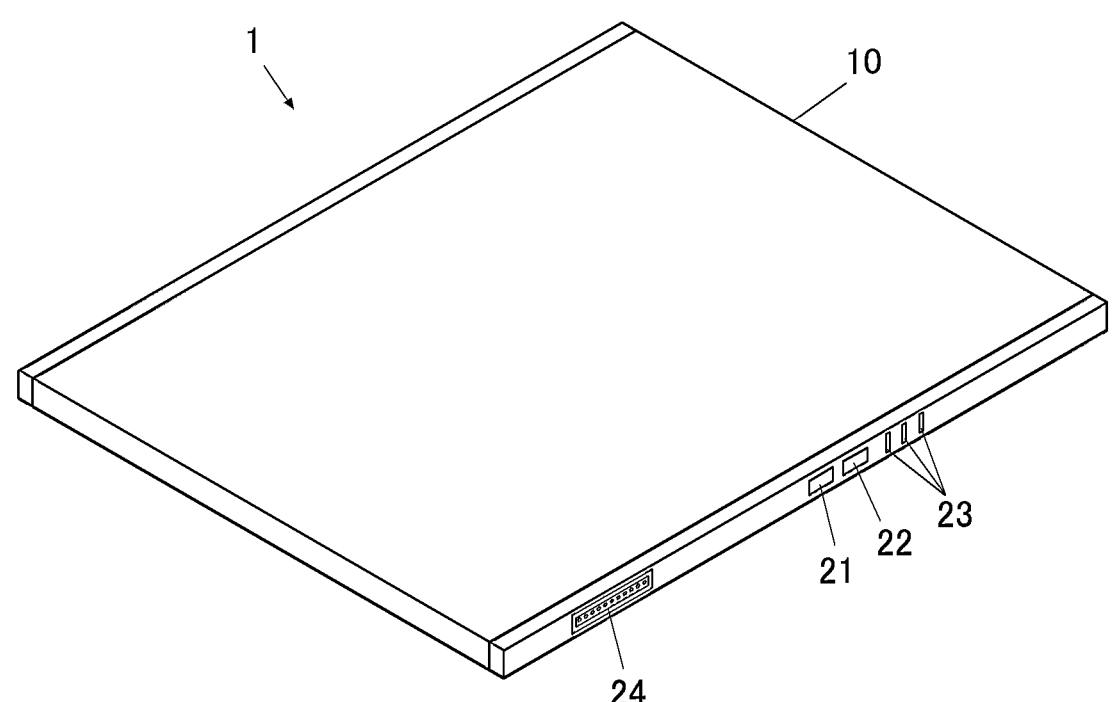
FIG. 1 is a perspective view illustrating an appearance of a radiation detection apparatus according to the present embodiment.
Figure 2:
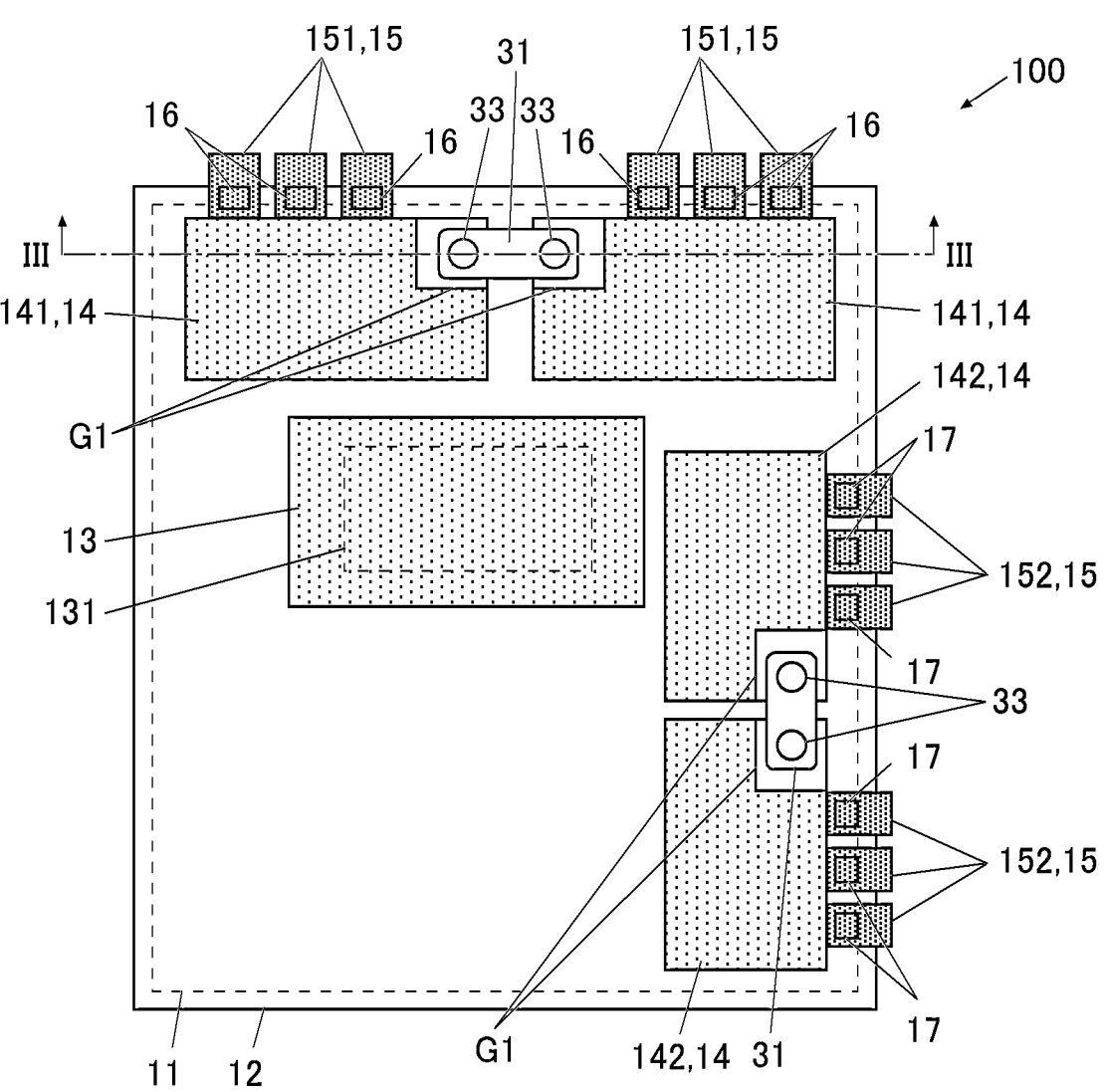
FIG. 2 is a plan view illustrating a configuration of an internal module.

As illustrated in FIG. 1, a radiation detection apparatus 1 according to the present embodiment includes a housing 10. As illustrated in FIG. 2, an internal module 100 is housed in the housing 10. The internal module 100 includes a radiation detector 11, a base 12, a control board 13, a plurality of circuit boards 14, a connection circuit board 15, a readout circuit 16, and a drive circuit 17.

The radiation detection apparatus 1 further includes, on an outer surface of the housing 10, a power switch 21, an operation switch 22, an indicator 23, and a connector 24 (see FIG. 1).

The housing 10 is formed of, for example, a carbon fiber reinforced plastics (CFRP). The housing 10 is divided into a box-shaped irradiation surface-side exterior and a rear surface-side exterior serving as a cover body. The irradiation surface-side exterior has a front surface and side surfaces that are radiation irradiation surfaces. The irradiation surface-side exterior and the rear surface-side exterior are, for example, screwed together and can be easily separated from each other. A waterproof member such as a packing (not illustrated) is provided at a joint between the irradiation surface-side exterior and the rear surface-side exterior so that liquid does not enter the inside of the housing 10.

The radiation detector 11 is formed by, for example, stacking and sealing a scintillator and a flexible thin film transistor (TFT). The flexible TFT includes a plurality of semiconductor elements and a plurality of TFTs arranged in a matrix on an imaging surface of the board. The board has flexibility. The TFT is a switch element. The imaging surface of the board is a surface on a side to be irradiated with radiation.

In the radiation detector 11, when radiation is emitted, first, the scintillator emits light corresponding to the intensity of the radiation. Next, the semiconductor element (photodiode) on the flexible TFT converts the light emitted by the scintillator into an electrical charge, and outputs the electrical charge as a signal to the connection circuit board 15.

The base 12 is a support substrate that supports the radiation detector 11 and boards such as the control board 13 and the plurality of circuit boards 14. The base 12 supports the radiation detector 11 on a first surface and the circuit boards 14 on a second surface opposite to the first surface. The base 12 is formed of a conductive member (for example, Mg). The base 12 may be fixed to the inner surface of the housing 10 with an adhesive agent or a gluing agent.

Alternatively, a positioning member (not illustrated) may be provided between the housing 10 and the base 12 so that the base 12 does not move.

The control board 13 includes a processing circuit 131. The processing circuit 131 includes a CPU, a ROM, a RAM, a communicator, and the like. The processing circuit 131 controls driving of the radiation detector 11 and processes a signal read from the radiation detector 11. Specifically, the processing circuit 131 generates image data from the signal read from the radiation detector 11, and outputs the image data to a console or the like (not illustrated).

The plurality of circuit boards 14 are boards that relay electrical connection between the radiation detector 11 and the processing circuit 131. Note that the plurality of circuit boards 14 may directly connect the radiation detector 11 and the processing circuit 131. The plurality of circuit boards 14 may indirectly connect the radiation detector 11 and the processing circuit 131 via another member. The plurality of circuit boards 14 process, for example, a signal read from the radiation detector 11.

The plurality of circuit boards 14 include a plurality of SIF boards 141 and a plurality of GIF boards 142.

The connection circuit board (COF: Chip On Film) 15 is a flexible board and connects the radiation detector 11 and the circuit board 14. The connection circuit board 15 includes a connection circuit board (S-COF) 151 and a connection circuit board (G-COF) 152. The readout circuit 16 is provided on the connection circuit board 151. The drive circuit 17 is provided on the connection circuit board 152.

The connection circuit board (S-COF) 151 is connected to the SIF board 141.

The connection circuit board (G-COF) 152 is connected to the GIF board 142.

The readout circuit (ROIC: Readout Integrated Circuit) 16 is a circuit that reads out a signal from the radiation detector 11.

The drive circuit (GDIC: Gate Driver Integrated Circuit) 17 is a circuit that drives the radiation detector 11.

Next, an example of a method of attaching the circuit boards 14 to the base 12 will be described with reference to FIG. 3 and FIG. 4.

Each of the plurality of circuit boards 14 is provided with a plurality of grounds for different purposes. The ground is set to a potential (reference potential) serving as a reference of circuit operation. Examples of the plurality of grounds include a ground (R-GND) G1, and a ground (G-GND) G2. The ground (R-GND) G1 is set to a potential serving as a reference for a digital signal such as an image. The ground (G-GND) G2 is set to a potential serving as a reference when an analog device is driven. Separating the ground G1 and the ground G2 can prevent noises from being unintentionally mixed with each other. In the present embodiment, the ground G1 is referred to as a first ground electrode of the present invention, and the ground G2 is referred to as a second ground electrode of the present invention. As described above, the ground G1 and the ground G2 are different in the electrical system. Note that the ground G1 and the ground G2 may have the same potential or different potentials.

In addition, the ground G1 and the ground G2 may be different electrical systems, also in connection with the outside of the radiation detection apparatus 1. Alternatively, a configuration may be adopted in which a single ground is used for connection with the outside, and the ground is separated into a plurality of electrical systems, such as a ground G1 and a ground G2, in a circuit inside the radiation detection apparatus 1.

Each of the SIF board 141 and the GIF board 142 is provided with a ground G1.

Figure 3:
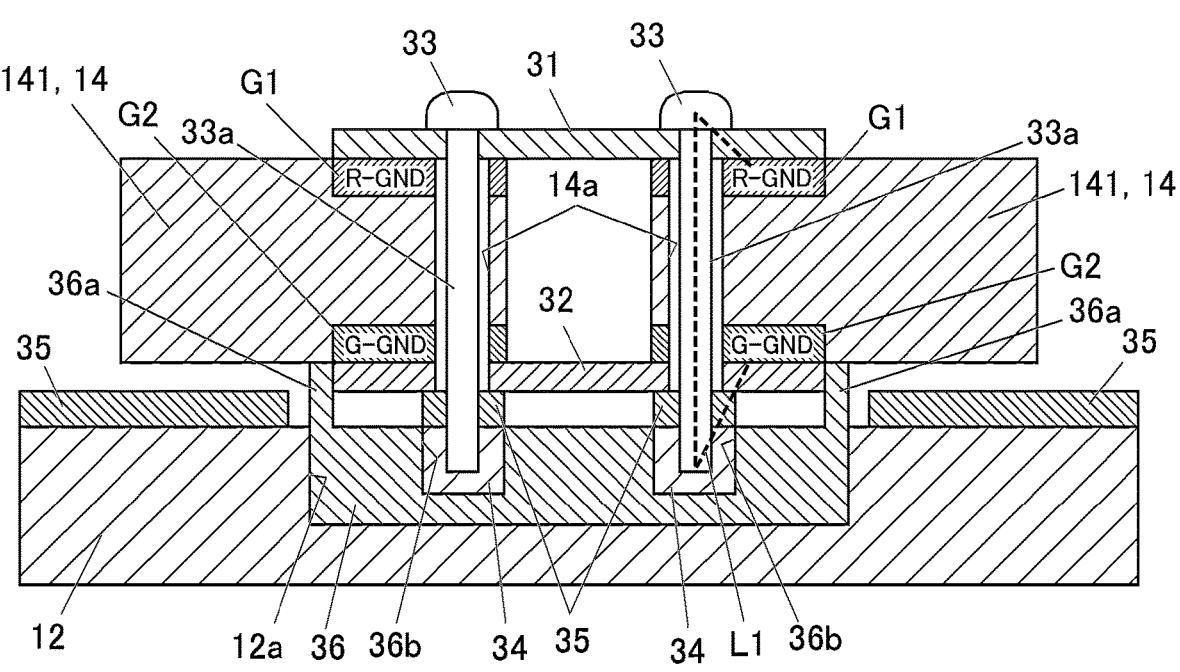
FIG. 3 is a cross-sectional view of the internal module taken along line III-III in FIG. 2.

The ground G1 is provided on the first surface of the circuit board 14, as illustrated in FIG. 2 and FIG. 3. Here, the first surface is a surface (a top surface in the drawing) opposite to a surface facing the base 12.

The SIF board 141 is provided with a ground G2. Note that the GIF board 142 may also be provided with a ground G2.

As illustrated in FIG. 3, the ground G2 is provided on a second surface of the circuit board 14 opposite to the first surface. Here, the second surface is a surface (a bottom surface in the drawing) facing the base 12.

The ground G1 and ground G2 on a circuit board 14 are arranged so as to face the ground G1 and ground G2 provided on a circuit board 14 adjacent thereto, respectively.

The grounds G1 are connected to each other between the adjacent circuit boards 14 by a first connecting member 31. The grounds G2 are connected to each other between the adjacent circuit boards 14 by a second connecting member 32. With the above-described configuration, the grounds G1, G2 can be electrically connected to each other between the adjacent circuit boards 14, so that the same potential between the circuit boards 14 can be stabilized.

The grounds of the same electrical system on the SIF board 141 and the GIF board 142 which are adjacent to each other may be connected to each other. Although the SIF board 141 and the GIF board 142 have different functions, the ground area can be increased by connecting the grounds of the same electric system. The large ground area makes it possible to further improve noise immunity.

As illustrated in FIG. 3, the first connecting member 31, the second connecting member 32, and the circuit board 14 are attached to the base 12 by one attachment screw 33. That is, the attachment screw 33 functions as an attachment member of the present invention for attaching the first connecting member 31, the second connecting member 32, and the circuit board 14 to the base 12. The attachment screw 33 is formed of, for example, a conductive material such as metal.

As illustrated in FIG. 3, the attachment screw 33 is attached to the base 12 via an engaging member 34. This causes the engaging member 34 to be electrically connected to the ground G1 via the first connecting member 31 and the attachment screw 33. Note that the attachment screw 33 is inserted through a screw hole 14a provided in the circuit board 14 and engages with the engaging member 34. Since an outer diameter of the screw hole 14a is larger than an outer diameter of screw threads 33a of the attachment screw 33, the attachment screw 33 and the circuit board 14 are not in contact with each other. This prevents the ground G1 and the ground G2 provided on the circuit board 14 from being electrically connected to each other via the attachment screw 33.

On the other hand, a first insulating member 35 is provided between the engaging member 34 and the second connecting member 32. The first insulating member 35 is formed of an insulating material such as a resin. This prevents the ground G2 and the engaging member 34 from being electrically connected to each other. Therefore, the ground G1 electrically connected to the engaging member 34 and the ground G2 are also prevented from being electrically connected to each other (see a broken line L1 in the drawing).

A second insulating member 36 is provided between the engaging member 34 and the base 12. The second insulating member 36 is formed of an insulating material such as a resin. This prevents the engaging member 34 and the base 12 from being electrically connected to each other. Therefore, the ground G1 electrically connected to the engaging member 34 and the base 12 are also prevented from being electrically connected to each other.

As described above, in the present embodiment, the first insulating member 35 prevents electrical connection between the ground G2 and the engaging member 34, and the second insulating member 36 prevents electrical connection between the engaging member 34 and the base 12. That is, the first insulating member 35 and the second insulating member 36 function as an insulating member of the present invention that blocks the electrical connection between the ground G2 and the base 12. The first insulating member 35 and the second insulating member 36 are provided between the second connecting member 32 and the base 12.

The second insulating member 36 is provided with protrusions 36a that regulate the position of the second connecting member 32. The protrusions 36a protrude upward at both ends in the longitudinal direction of the second connecting member 32. This prevents the second connecting member 32 from being displaced and coming into contact with the attachment screw 33 or the base 12.

Figure 4:
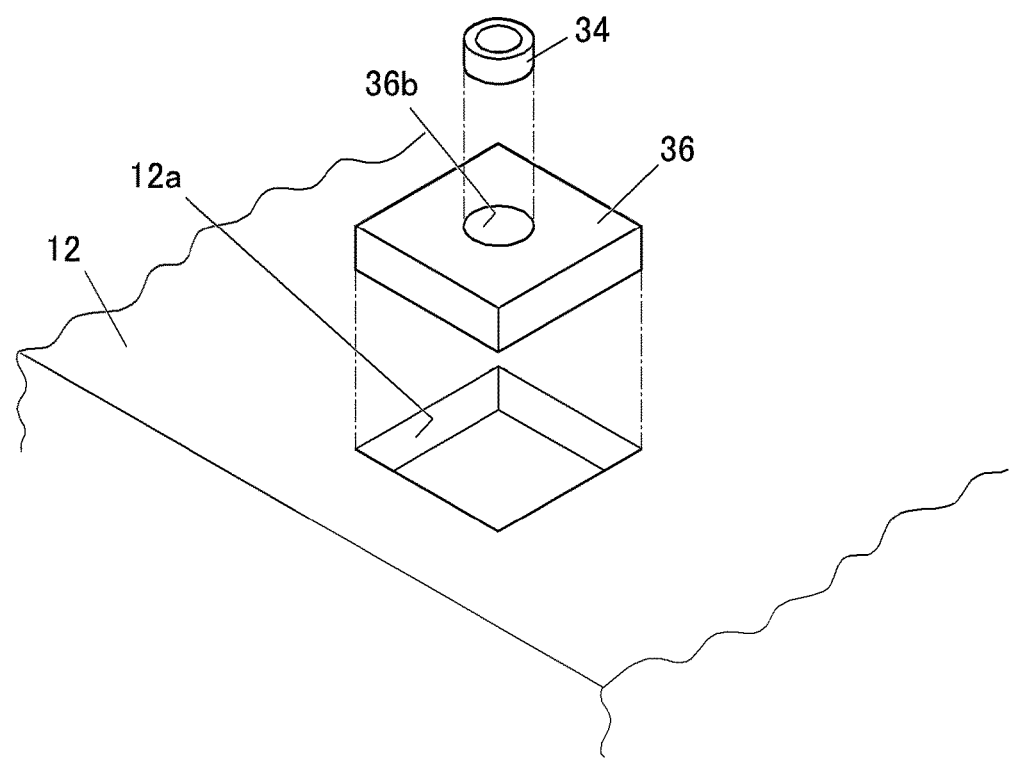
FIG. 4 is a diagram illustrating an example of a state in which an engaging member and a second insulating member are bonded to a base.

As illustrated in FIG. 4, the engaging member 34 is formed into a hollow cylindrical shape. The engaging member 34 is fitted into a hole 36b in the second insulating member 36 by a method such as bonding or press-fitting. An inner surface of the engaging member 34 is provided with female threads, and the female threads are engageable with the screw threads 33a of the attachment screw 33. The second insulating member 36 into which the engaging member 34 is fitted is bonded to a recess 12a provided in the base 12. As illustrated in FIG. 3, a height of the engaging member 34 is shorter than a thickness of the second insulating member 36. This prevents the engaging member 34 from contacting the base 12. Since the engaging member 34 and the base 12 are not in contact with each other, they are prevented from being electrically connected to each other.

As described above, the radiation detection apparatus 1 according to the present embodiment includes the radiation detector 11 that detects radiations, the conductive base 12 that supports the radiation detector 11, the circuit boards 14 each that include the first ground electrode (the ground (R-GND) G1) and the second ground electrode (the ground (G-GND) G2) different from the first ground electrode and processes a signal read from the radiation detector 11, and the insulating members (the first insulating member 35 and the second insulating member 36) that block the electrical connection between the second ground electrodes and the base 12.

Therefore, according to the radiation detection apparatus 1 of the present embodiment, it is possible to prevent electrical connection between the grounds for different purposes among the plurality of grounds of the circuit boards 14 via the conductive base 12. This makes it possible to prevent the occurrence of image unevenness, even in a configuration in which a plurality of potentials for different purposes are provided on the circuit board 14.

According to the radiation detection apparatus 1 of the present embodiment, the first ground electrode and the second ground electrode have the same potential and different electrical systems.

Therefore, according to the radiation detection apparatus 1 of the present embodiment, it is possible to prevent electrical connection between the grounds having the same potential and different electric systems due to different purposes via the conductive base 12. This makes it possible to prevent noises from being unintentionally mixed with each other, and to prevent the occurrence of image unevenness.

The radiation detection apparatus 1 according to the present embodiment includes the first connecting member 31 that connects the first ground electrodes among the plurality of circuit boards 14 and the second connecting member 32 that connects the second ground electrodes among the plurality of circuit boards 14.

Therefore, according to the radiation detection apparatus 1 of the present embodiment, the grounds G1, G2 can be electrically connected to each other between the adjacent circuit boards 14. This makes it possible to stabilize the same potential between the circuit boards 14.

The radiation detection apparatus 1 according to the present embodiment includes the attachment members (the attachment screws 33) that attach the first connecting member 31, the second connecting member 32, and the circuit boards 14 to the base 12.

Therefore, according to the radiation detection apparatus 1 of the present embodiment, each connecting member and the circuit boards 14 can be fastened together to the base 12 and brought into pressure contact with each other using the attachment screws 33. This makes it possible to ensure reliable electrical connection between the grounds G1, G2 between the adjacent circuit boards 14.

According to the radiation detection apparatus 1 of the present embodiment, the first ground electrode is provided on the first surface of the circuit board 14, the second ground electrode is provided on the second surface of the circuit board 14 opposite to the first surface, and the first connecting member 31, the second connecting member 32, and the circuit board 14 are attached to the base 12 by one attachment member.

Therefore, according to the radiation detection apparatus 1 of the present embodiment, it is possible to arrange the grounds using both surfaces of the circuit board 14. This makes it possible to reduce the area of the circuit board 14 and reduce the weight of the apparatus. Furthermore, since two grounds can be attached by one attachment screw 33, the number of components can be reduced.

According to the radiation detection apparatus 1 of the present embodiment, the attachment member is attached to the base 12 via the engaging member 34, and the insulating member is provided between the second connecting member 32 and the base 12.

Therefore, according to the radiation detection apparatus 1 of the present embodiment, it is possible to prevent the second connecting member 32 and the base 12 from being electrically connected to each other. This makes it possible to prevent the ground G2 electrically connected to the second connecting member 32 and the base 12 from being electrically connected to each other.

According to the radiation detection apparatus 1 of the present embodiment, the attachment member is attached to the base 12 via the engaging member 34, and the insulating member is provided between the engaging member 34 and the base 12.

Therefore, according to the radiation detection apparatus 1 of the present embodiment, it is possible to prevent the engaging member 34 and the base 12 from being electrically connected to each other. This makes it possible to also prevent the ground G1 electrically connected to the engaging member 34 and the base 12 from being electrically connected to each other.

Although, in the above, an embodiment of the present invention have been described in detail, the present invention is not limited thereto, but can be modified within a range of not departing from its scope.

Modification Example 1

Figure 5:
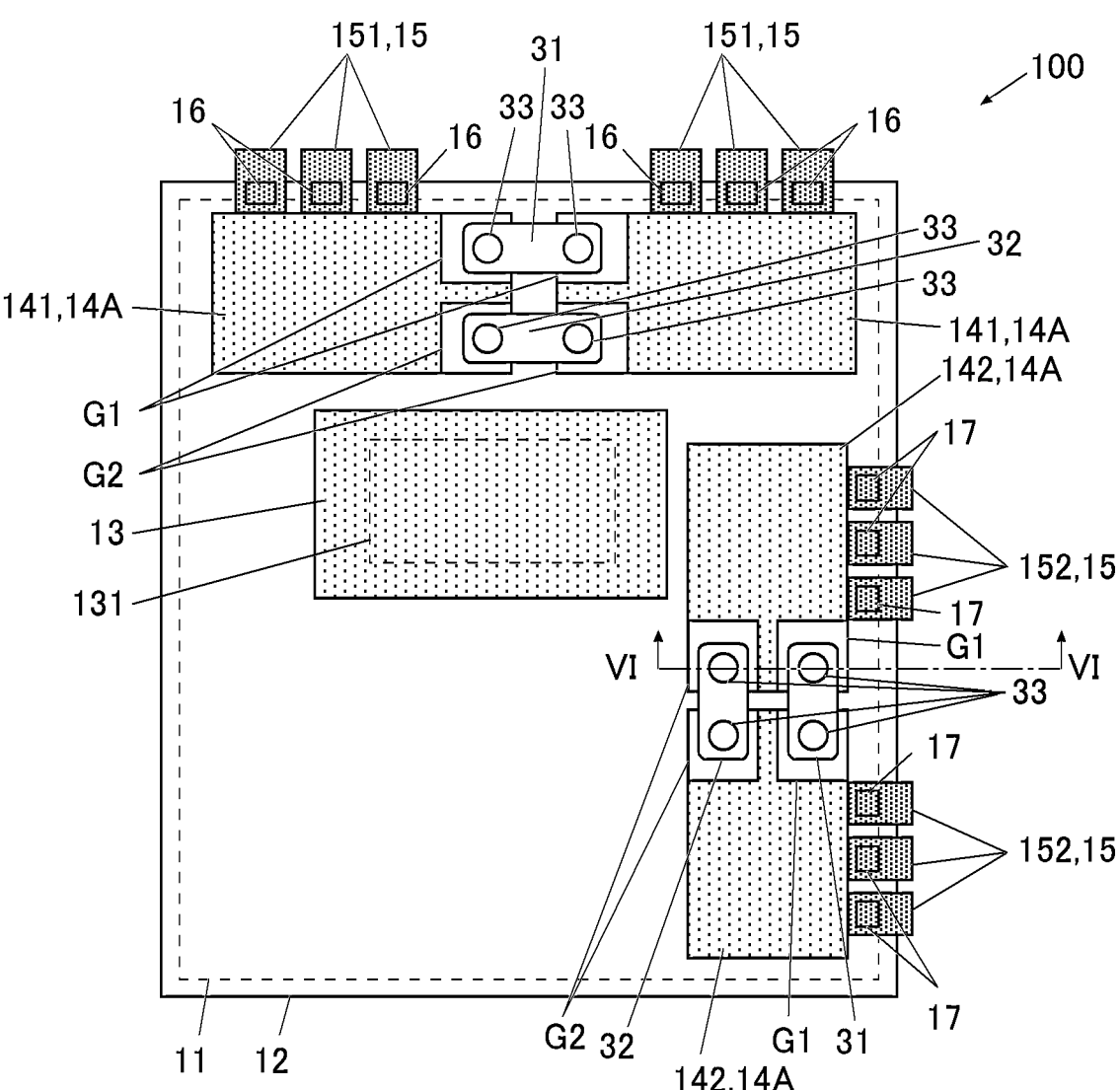
FIG. 5 is a plan view illustrating a configuration of an internal module according to modification example 1.
Figure 6:
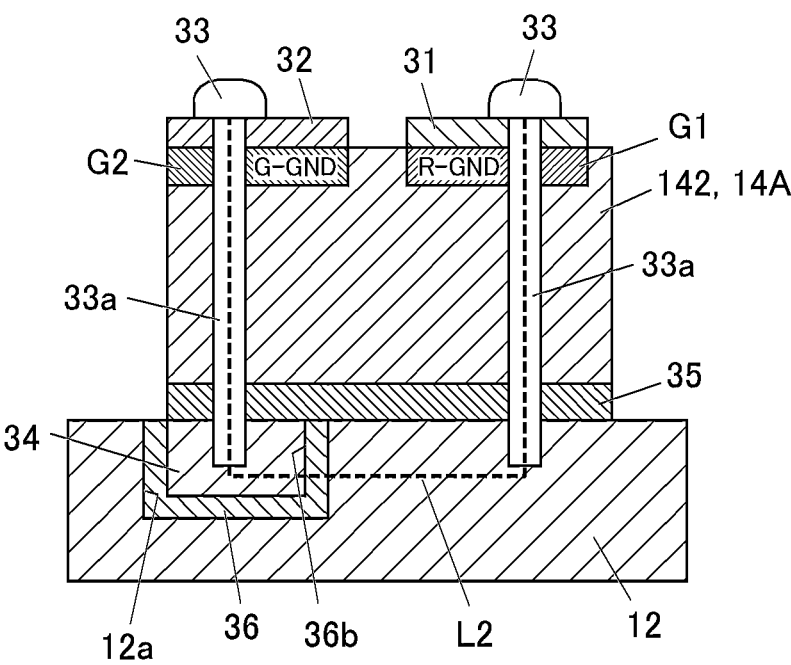
FIG. 6 is a cross-sectional view of the internal module taken along line VI-VI in FIG. 5.

For example, in the above-described embodiment, the ground (R-GND) G1 is provided on the first surface of the circuit board 14 and the ground (G-GND) G2 is provided on the second surface of the circuit board 14, but the present invention is not limited thereto. For example, as illustrated in FIG. 5 and FIG. 6, both of a ground G1 and a ground G2 may be provided on a first surface of a circuit board 14A.

That is, the ground G1 and the ground G2 are provided on the first surface of the circuit board 14A according to Modification Example 1. The ground G1 and ground G2 on a circuit board 14A are arranged so as to face the ground G1 and ground G2 provided on a circuit board 14A adjacent thereto, respectively.

The grounds G1 are connected to each other between the adjacent circuit boards 14A by a first connecting member 31. The grounds G2 are connected to each other between the adjacent circuit boards 14A by a second connecting member 32. With the above-described configuration, the grounds G1, G2 can be electrically connected to each other between the adjacent circuit boards 14A. This makes it possible to stabilize the same potential between the circuit boards 14A.

The first connecting member 31 and the circuit board 14A are attached to a base 12 by one attachment screw 33. Furthermore, the second connecting member 32 and the circuit board 14A are attached to the base 12 by one attachment screw 33.

As illustrated in FIG. 6, the attachment screw 33 for attaching the first connecting member 31 to the base 12 is directly attached to the base 12. This causes the base 12 to be electrically connected to the ground G1 via the attachment screw 33. Furthermore, as illustrated in FIG. 6, the attachment screw 33 for attaching the second connecting member 32 to the base 12 is attached to the base 12 via an engaging member 34. This causes the engaging member 34 to be electrically connected to the ground G2 via the attachment screw 33.

On the other hand, a first insulating member 35 is provided between the engaging member 34 and the circuit board 14A. The first insulating member 35 is formed of an insulating material such as a resin.

A second insulating member 36 is provided between the engaging member 34 and the base 12. The second insulating member 36 is formed of an insulating material such as a resin. This prevents the engaging member 34 and the base 12 from being electrically connected to each other. Therefore, the ground G2 electrically connected to the engaging member 34 and the base 12 are also prevented from being electrically connected to each other (see a broken line L2 in the drawing).

That is, in Modification Example 1, the second insulating member 36 prevents electrical connection between the engaging member 34 electrically connected to the ground G2 and the base 12. That is, the second insulating member 36 functions as an insulating member of the present invention that blocks the electrical connection between the ground G2 and the base 12. Furthermore, the second insulating member 36 is provided between the second connecting member 32 and the base 12.

The engaging member 34 is formed into a hollow cylindrical shape in the same manner as in the embodiment. The engaging member 34 is fitted into a hole 36b in the second insulating member 36 by a method such as bonding or press-fitting. An inner surface of the engaging member 34 is provided with female threads, and the female threads are engageable with screw threads 33a of the attachment screw 33. The second insulating member 36 into which the engaging member 34 is fitted is bonded to a recess 12a provided in the base 12 in the same manner as in the embodiment. As illustrated in FIG. 6, a height of the engaging member 34 is shorter than a thickness of the second insulating member 36. This prevents the engaging member 34 from contacting the base 12. Since the engaging member 34 and the base 12 are not in contact with each other, they are prevented from being electrically connected to each other.

As described above, according to the configuration of Modification Example 1, it is possible to prevent electrical connection between the ground G2 and the base 12. This makes it possible to prevent electrical connection between the grounds for different purposes via the conductive base 12, and to prevent the occurrence of image unevenness.

Modification Example 2

Figure 7:
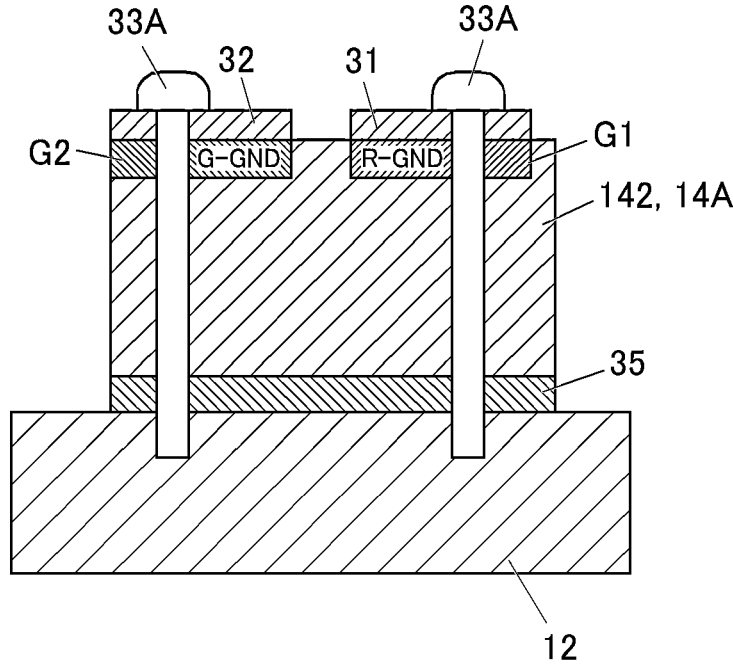
FIG. 7 is a cross-sectional view illustrating a configuration of an internal module according to modification example 2.
Figure 8:
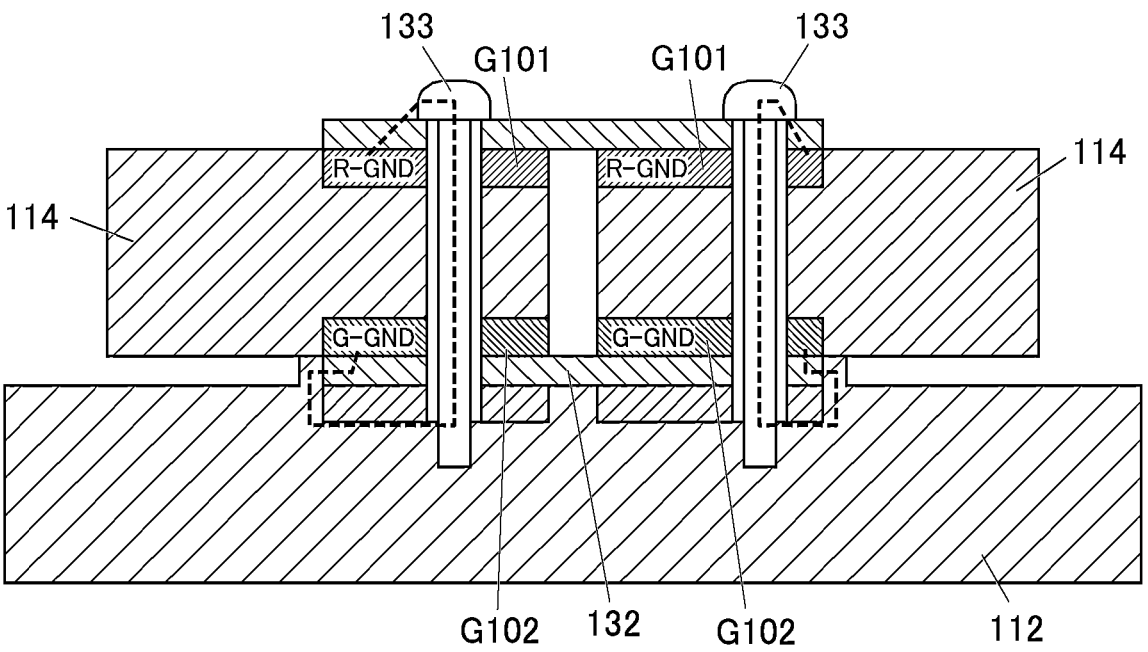
FIG. 8 is a cross-sectional view illustrating a configuration of an internal module according to a conventional technique.

In the above-described embodiment and Modification Example 1, the configuration in which the attachment screw 33 formed of a conductive material such as metal is used as the attachment member of the present invention has been described as an example, but the present invention is not limited thereto. For example, an attachment screw 33A formed of an insulating material such as a resin may be used. FIG. 7 illustrates a configuration of Modification Example 2 in which the attachment screws 33A are applied to the configuration of Modification Example 1 (the configuration in which the ground G1 and the ground G2 are provided on a first surface of a circuit board 14A).

In the case of FIG. 7, the base 12 is not electrically connected to the ground G1 or the ground G2 via the attachment screw 33A. Therefore, it is not necessary to attach the attachment screw 33 to the base 12 via the engaging member 34 and to provide the second insulating member 36 between the engaging member 34 and the base 12 in the same manner as in the above-described embodiment and Modification Example 1. Thus, as illustrated in FIG. 7, each attachment screw 33A is directly attached to the base 12. The attachment screws 33A attach a first connecting member 31 and a second connecting member 32 to the base 12. That is, in the configuration of Modification Example 2, it is not necessary to provide the engaging member 34 and the second insulating member 36 as compared with the configuration of Modification Example 1, and therefore, the number of components can be reduced.

As described above, in Modification Example 2, the attachment screw 33A functions as the insulating member of the present invention that blocks the electrical connection between the ground G2 and the base 12.

As described above, according to the configuration of Modification Example 2, the attachment member (the attachment screw 33A) is formed of an insulating material. Therefore, it is not necessary to provide the engaging member 34 and the second insulating member 36, and therefore, the number of components can be reduced.

The detailed configurations and operations of the components constituting the radiation detection apparatus can be appropriately changed within a range of not departing from the scope of the present invention.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A radiation detection apparatus, comprising:
   a radiation detector that detects radiations;
   a conductive base that supports the radiation detector;
   at least one circuit board that includes a first ground electrode and a second ground electrode different from the first ground electrode, and processes a signal read from the radiation detector; and
   an insulating member that blocks an electrical connection between the second ground electrode and the conductive base.

2. The radiation detection apparatus according to claim 1, wherein the first ground electrode and the second ground electrode have the same potential and different electrical systems.

3. The radiation detection apparatus according to claim 1, wherein the at least one circuit board comprises a plurality of circuit boards, each circuit board of the plurality of circuit boards includes a first ground electrode and a second ground electrode different from the first ground electrode, the radiation detection apparatus further comprises:
   a first connecting member that connects first ground electrodes among the plurality of circuit boards; and
   a second connecting member that connects second ground electrodes among the plurality of the circuit boards.

4. The radiation detection apparatus according to claim 3, further comprising an attachment member that attaches the first connecting member, the second connecting member, and the plurality of circuit boards to the base.

5. The radiation detection apparatus according to claim 4, wherein
   each first ground electrode is provided on a first surface of each circuit board,
   each second ground electrode is provided on a second surface of each circuit board opposite to the first surface, and
   the first connecting member, the second connecting member, and each circuit board are attached to the conductive base by the attachment member.

6. The radiation detection apparatus according to claim 4, further comprising an engaging member, wherein
   the attachment member is attached to the conductive base via the engaging member, and
   the insulating member is provided between the second connecting member and the conductive base.

7. The radiation detection apparatus according to claim 4, further comprising an engaging member, wherein
   the attachment member is attached to the conductive base via the engaging member, and
   the insulating member is provided between the engaging member and the conductive base.

8. The radiation detection apparatus according to claim 4, wherein the attachment member comprises an insulating material.

* * * * *